United States Patent [19]

Soodak et al.

[11] 4,227,814
[45] Oct. 14, 1980

[54] OPTICAL DENSITY DETECTOR

[75] Inventors: Charles Soodak, Silver Spring; Rene G. Lamadrid, Bethesda; David Lohr, Ellicott City, all of Md.

[73] Assignee: Baxter Travenol Laboratories, Inc., Deerfield, Ill.

[21] Appl. No.: 8,274

[22] Filed: Feb. 1, 1979

[51] Int. Cl.³ .............................................. G01N 21/85
[52] U.S. Cl. ...................................... 356/410; 356/39; 356/414; 250/576
[58] Field of Search ...................................... 356/39–41, 356/410, 414, 436, 440, 246; 250/573–576

[56] References Cited

U.S. PATENT DOCUMENTS

| | | | |
|---|---|---|---|
| 2,706,927 | 4/1955 | Wood | 356/41 |
| 2,835,252 | 5/1958 | Mauchel | 356/39 X |
| 2,875,666 | 3/1959 | Parker et al. | 356/39 X |
| 3,527,542 | 9/1970 | Penhasi et al. | 356/39 X |
| 3,812,482 | 5/1974 | Clark | 356/39 X |
| 3,827,810 | 8/1974 | Codina | 356/410 X |
| 3,900,396 | 8/1975 | Lamadrid | 250/575 X |
| 3,935,876 | 2/1976 | Massie et al. | 356/39 X |
| 3,972,614 | 8/1976 | Johansen et al. | 356/40 X |

*Primary Examiner*—F. L. Evans
*Attorney, Agent, or Firm*—Robert A. Benziger; Paul C. Flattery; Thomas R. Vigil

[57] ABSTRACT

The optical detector is particularly adapted for use with an apparatus for separating blood into its components and is of the type including a centrifuge for centrifuging whole blood to separate same into the components thereof and of the type wherein plasma is withdrawn from the centrifuge through a flexible, light transmitting tubing and the spillover of red blood cells into the plasma withdrawn is monitored by the optical detector. The optical detector comprises a block having a slot across the top face thereof, the inner portion of the slot having a width less than the outer diameter of the tubing which is received in the slot such that when the tubing is pressed into the slot, it is squeezed from a circular cross section to an oval cross section to present two flat portions of the tubing adjacent opposite sidewalls of the slot. A first cavity is situated in the block behing a first sidewall of the slot and a second cavity is situated in the block behind a second sidewall of the slot. Apertures are provided in the sidewalls and light from a light source is directed along the axis of the apertures, through lenses in the cavities which seal the cavities from the slot and through the tubing in the slot from the first cavity to the second cavity where a photosensor is located. The photosensor is operable to generate an electrical signal which is indicative of the light sensed and which can be utilized for measuring the optical density of the plasma flowing through the tubing.

16 Claims, 3 Drawing Figures

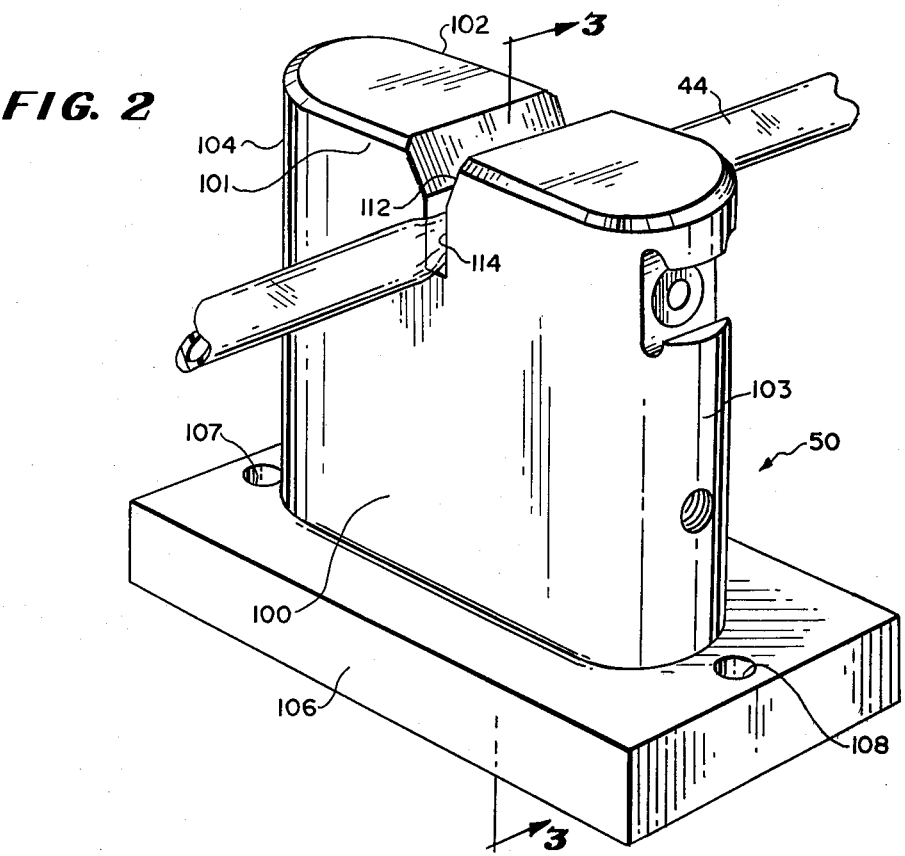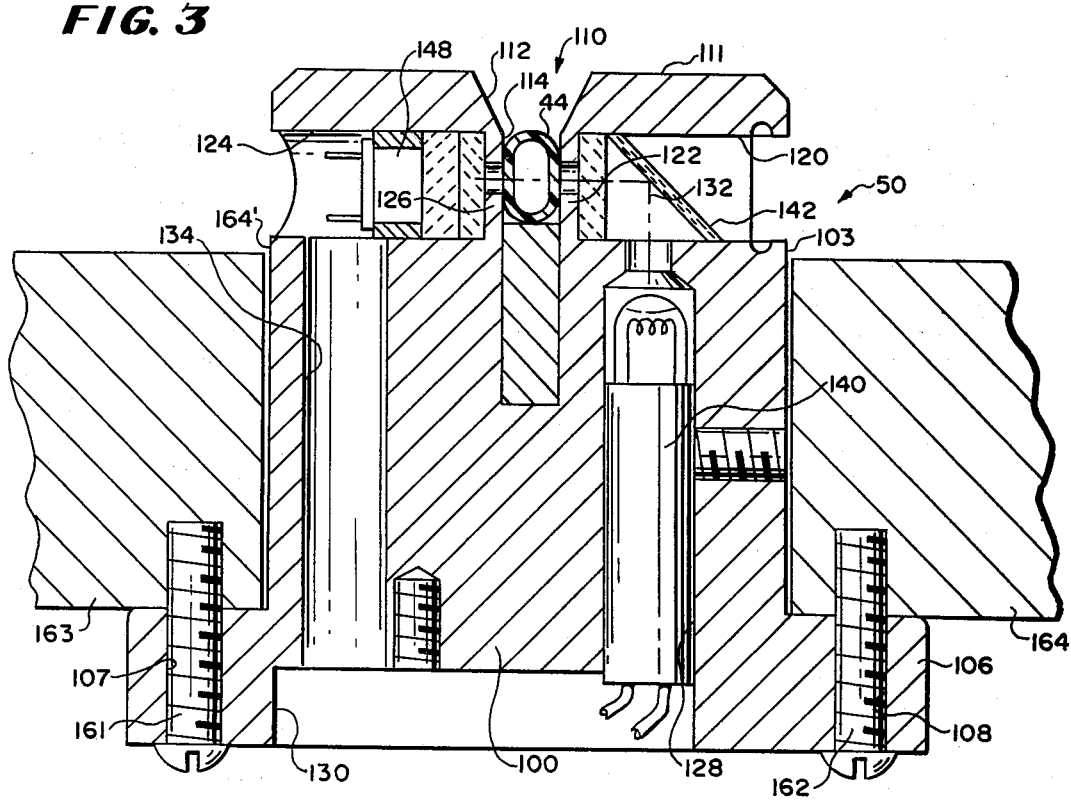

OPTICAL DENSITY DETECTOR

BACKGROUND OF THE INVENTION

1. Field of the Invention

The field of the invention is optical detectors for detecting changes in optical density of, i.e., light transmitted through, a liquid flowing through a tubing. More specifically, the present invention relates to an optical detector which is particularly useful in sensing red blood cells in plasma flowing through a tubing in an apparatus for separating whole blood into the components thereof.

2. Description of the Prior Art

Heretofore various optical detectors have been utilized for sensing changes in optical density of a liquid by sensing changes in the light transmitted through the liquid. Such optical detectors have included a light source and a light sensor. An example of one such optical sensor is disclosed in U.S. Pat. No. 3,900,396.

Oftentimes the liquid which is being monitored by the optical detector is passed through a chamber in the optical detector. This requires fluid seals between the tubing and the chamber in the detector.

In an apparatus for processing blood where it is desirable to maintain the blood in a sterile environment and make non-invasive optical measurements of the liquid, such as blood, it is desirable to provide an optical detector which can make optical measurements of light passed through the liquid in a flexible light transmitting tubing which has a generally circular cross section. However, the curved wall portions of the tubing refract and deflect light. Accordingly, it is important to provide means for establishing flat portions of the tubing in the area where light is directed through the tubing so that the light is not refracted or deflected by curved wall portions of the tubing.

Also, it is desirable to provide a simple, inexpensive detector which is highly reliable and highly sensitive so that accurate sensings of red blood cells mixed with plasma can be made by the detector. In this respect, it has been found to be important to provide an optical detector wherein the light source generates a minimum of heat and where the optical detector has means for dissipating any heat so generated so that such heat does not adversely affect the operation of a photosensor utilized in sensing light transmitted through the tubing.

Additionally, it is desirable to monitor the absorbance of blue green light at 550 nanometers wavelength by oxygenated hemoglobin to determine the presence of red blood cells in the plasma since the absorbance of light at that wavelength by other substances carried in the blood is minimal.

As will be described in greater detail hereinafter, the optical detector of the present invention provides a simple, inexpensive, reliable, efficient and highly sensitive optical detector which has a low power light source to minimize the generation of heat by the light source, which has a highly sensitive photosensor and which is constructed in a manner to dissipate heat so generated to prevent such heat from adversely affecting the operation of the photosensor utilized with the optical detector.

SUMMARY OF THE INVENTION

According to the invention there is provided an optical detector for sensing the change in optical density of a fluid flowing in a flexible, light transmitting tubing, said detector comprising a block having a slot across one face thereof, the inner portion of said slot having a width less than the outer diameter of the tubing which is received in said slot such that the tubing is squeezed from a circular cross section to an oval cross section with two respective flat portions adjacent opposite sidewalls of said slot, a first cavity in said block located behind a first sidewall of said slot and a second cavity in said block located behind a second sidewall of said slot, a first aperture in said first sidewall and a second aperture in said second sidewall, said apertures being coaxial, low power light generating means for directing light from said first cavity through said first aperture, through the flat portions of the tubing and through said second aperture into said second cavity and light sensing means in said second cavity for sensing the amount of light passed through the tubing and received in said second cavity and for generating an electrical signal which is indicative of the amount of light sensed and which can be utilized for measuring the optical density of the fluid flowing through the tubing, and said block being constructed in a manner to dissipate heat generated by said light generating means.

BRIEF DESCRIPTION OF THE DRAWINGS

FIG. 2 is a perspective elevational view of the optical detector of the present invention.

FIG. 3 is a vertical sectional view taken along line 3—3 of FIG. 2.

DESCRIPTION OF THE PREFERRED EMBODIMENTS

Figure 1:
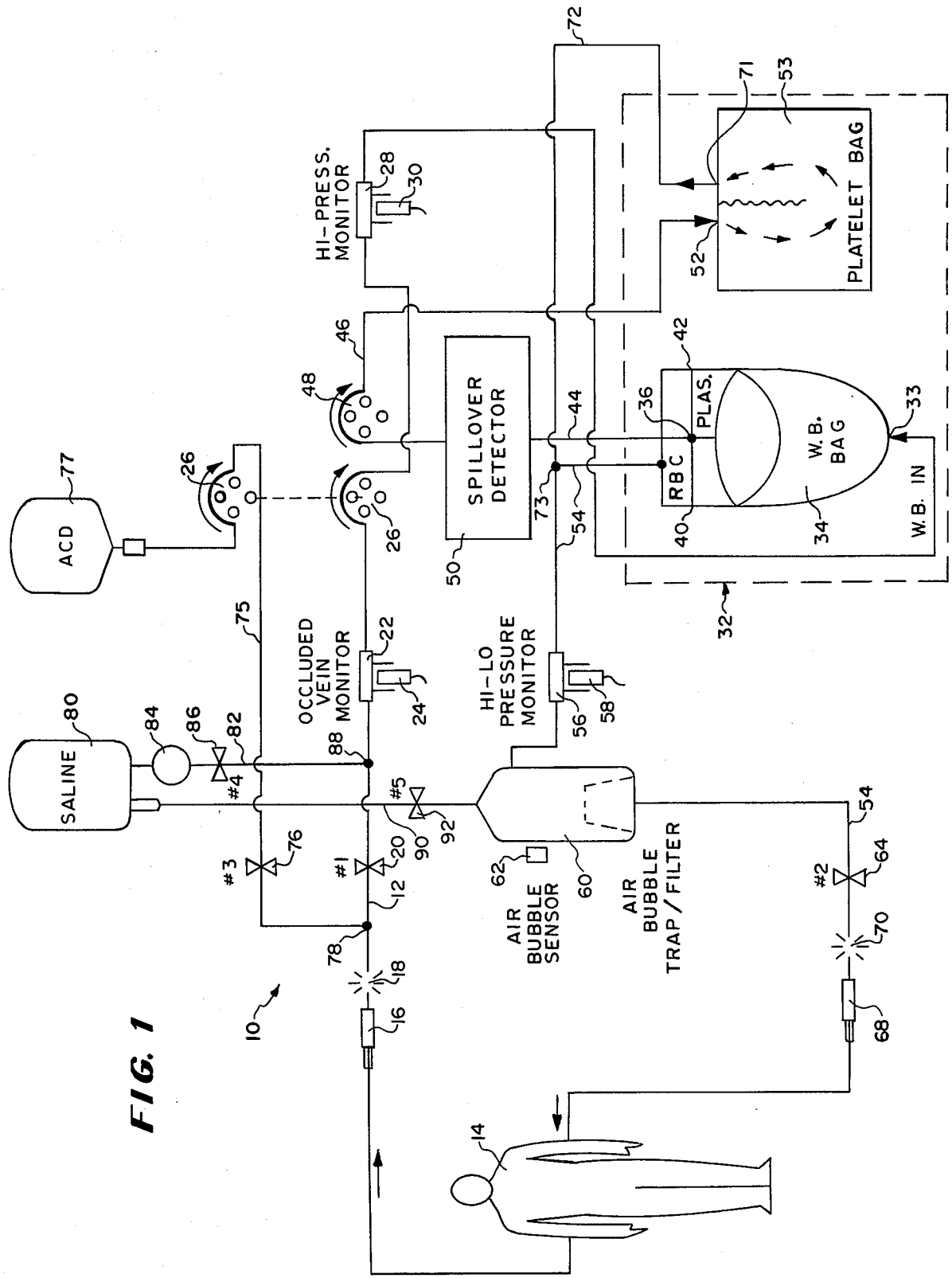
FIG. 1 is a schematic block diagram of a fluid circuit for an apparatus which is operable in separating whole blood into the components therreof and which utilizes the optical detector of the present invention.

Referring to the drawings in greater detail, in FIG. 1 there is illustrated a block schematic diagram of a fluid circuit of an apparatus 10 for separating whole blood into the components thereof and for collecting at least one component, e.g., platelets. As shown, the fluid circuit includes a first tubing 12 which is adapted to be coupled to a vein in one arm of a donor 14 by means of a hypodermic needle 16 which is injected into the one arm. For safety reasons, a fluid clamp 18 (shown schematically) is provided on the tubing 12. Also the first tubing 12 has associated therewith an electro-mechanically operated clamp 20 forming a first valve #1. The tubing 12 then has series coupled thereto an occluded vein monitor device 22 with an associated sensor 24. From the monitor device 22 the first tubing 12 extends over and forms part of a peristaltic pump 26 and is then series coupled to a high pressure monitor device 28 with an associated sensor 30. From the monitor device 28 the first tubing 12 extends into a centrifuge device 32 (shown schematically) and to a bottom inlet 33 of a first compartment or receptacle 34 which is identified as a whole blood bag and which defines therein a separation chamber in which whole blood is separated into its components.

The receptacle 34 has a first outlet 36 at the center thereof adjacent a zone in the receptacle 34 where platelet-rich plasma congregates. Receptacle 34 also has two outlets 40 and 42 at the upper corners thereof where red blood cells congregate. Outlet 36 provides not only an outlet for platelet-rich plasma but also a return inlet for platelet-rich plasma which is "contaminated" (mixed) with red blood cells when there is a spillover of red blood cells out of the first outlet 36.

The first outlet 36 of the first receptacle 34 is coupled by a second tubing 44 to a loop 46 thereof located exterior of the centrifuge device 32 and which loop 46 extends about and forms part of a peristaltic pump 48. Also, positioned adjacent a flexible light transmitting section of the tubing 44 in the loop 46 is an optical spillover detector 50 which includes an optical sensor for sensing a spillover of red blood cells mixed with platelet-rich plasma flowing out of the outlet 36, which is constructed in accordance with the teachings of the present invention and which will be described in greater detail hereinafter in connection with the description of FIGS. 2 and 3.

The second tubing 44 then goes back into the centrifuge device 32 and is coupled to an inlet 52 of a second compartment or receptacle 53 which is identified as a platelet bag and which defines a chamber therein in which platelets are separated from plasma.

A tubing 54 is connected to the outlets 40 and 42 of the receptacle 34 for returning the blood fluid to the donor through a high/low pressure monitor device 56 with associated sensor 58 and an air bubble trap/filter 60 and associated air bubble sensor 62. As shown, the monitor device 56 and the filter 60 are coupled in series in the third tubing 54. The sensor 62 can be optical or ultrasonic. Also another electro-mechanically operated clamp 64 is associated with a portion 66 of the tubing 54 coming out of the air bubble trap/filter 60 and defines a second valve #2.

The end of the third tubing 54 is connected to a hypodermic needle 68 adapted for injection into the other arm of the donor 14, and, if desired for safety reasons, a fluid clamp 70 (shown schematically) can be provided on tubing 54 ahead of the needle 68.

The fluid circuit of the apparatus 10 also includes a container 74 of anticoagulant such as Anticoagulant Citrate Dextrose (ACD) which is coupled by a fourth tubing 75 extending about (and forming part of) the peristaltic pump 26 and past an electro-mechanically operated clamp 76 defining a third valve #3 to a junction 78 with the first tubing 12 between the needle 16 and valve #1. The container 72 is typically a flexible plastic container.

With this arrangement of the first tubing 12 and the fourth tubing 75 passing over the same peristaltic pump 26, the mixing of anticoagulant with whole blood and the withdrawing of whole blood from the donor is achieved essentially simultaneously. Also, the ratio of the cross-sectional area of the interior of the tubing 12 to the cross-sectional area of the interior of the tubing 75 is chosen to obtain a desired mixture of anticoagulant to whole blood. This ratio is preferably 8 to 1 thereby to obtain an 8 to 1 ratio of whole blood to anticoagulant.

The fluid circuit of the apparatus 10 further includes a container 80 of saline solution which is connected by means of a fifth tubing 82 through a drip chamber 84 and an electro-mechanically operated clamp 86 defining a fourth valve #4 to the first tubing 12 at a junction 88 between valve #1 and the occluded vein monitor device 22. The container 80 of saline solution is also coupled by means of a sixth tubing 90 through an electromechanically operated clamp 92 forming a fifth valve #5 to the top of the air bubble trap/filter 60. The container 80 is typically a flexible plastic container.

The pressure monitor devices 22, 28 and 56 each include a flow through chamber series connected in associated tubing 12 or 54, and an air filled closed chamber having a flexible diaphragm forming part of one wall of the flow through chamber and an outer wall which is situated adjacent the associated sensor 24, 30 or 58 which are pressure transducers and which sense changes in pressure on the outer wall.

It will be appreciated that platelets are removed from the plasma in the platelet separation bag 53 thereby to provide platelet-poor, and essentially platelet free, plasma at the outlet 71 from the platelet bag 53.

The operation of the apparatus 10 for processing whole blood through the fluid circuit and for collecting platelets separated from the whole blood now will be described briefly with reference to FIG. 1.

Valve #1 is first opened to allow saline to purge the input needle 16 prior to injection in the patient 14. Then valves #1, #3 and #5 are closed. Valves #2 and #4 are open.

Then saline is pumped by the first pump 26 through the fluid circuit of the apparatus 10 until no more air bubbles are sensed by the air bubble sensor 62, i.e., until saline is sensed.

Next, the second pump 48 is started and saline is pumped through the platelet receptacle 53. Since the centrifuge device 32 is not running at this time, the receptacles 34 and 55 are not filled to capacity. Air is expelled through the needle 68.

After a short time, e.g., one to five minutes, the platelet receptacle/bag 53 will be filled, all air expelled and saline fills the entire system, i.e., the fluid circuit of the apparatus 10 up to valve #2. When saline is sensed by detector 62, valve #2 is closed and valve #5 is opened. After a period of recirculation of saline, pumps 26 and 48 are stopped and valve #2 is opened.

Parenthetically, during this priming operation, the air bubble sensor 62 is checked when air bubbles are flowing through the air bubble trap/filter 60 to make sure that sensor 62 is working properly and then later, sensor 62 is checked to make sure there are no more bubbles after the system is filled with saline.

Now two venipunctures are made with the needles 16 and 68 to insert the needles 16 and 68 into the arms of the donor 14, and valves #1, #3 and #5 are open and valve #2 is closed.

With the needles 16 and 68 connected to the veins of a donor and the system full of saline, the pumps 26 and 48 are started and whole blood is pumped into the system and into the centrifuge device 32.

It will be noted that the tubings 12, 44 and 54 extending into the centrifuge device 32 may be combined in an umbilicus which is rotated at a speed ½ the speed of the centrifuge device so that twisting is avoided and no fluid seals are required.

This arrangement and operation of the centrifuge device 32 is more fully described in a co-pending application Ser. No. 657,187 filed Feb. 11, 1976 and entitled: CENTRIFUGAL LIQUID PROCESSING SYSTEM.

When approximately 120 milliliters of whole blood has been pumped into the fluid circuit of the apparatus 10, most of the saline solution will have been pumped back into the container 80. Valve #2 is now opened so that processed blood fluid mixed with some saline solution can now be returned to the patient.

After starting pumps 26 and 48 no further operator attention is required until the plasma treatment run has been completed and the operator is ready to return the recombined blood components to the donor. Also, during the run, the spillover detector 50 operates the pumps 26 and 48 in such a manner as to prevent red blood cell contamination of the plasma being withdrawn from the receptacle 34. The manner in which this is accomplished is explained in more detail in a co-pending application Ser. No. 843,222 filed Oct. 18, 1977 and entitled: METHOD AND APPARATUS FOR PROCESSING BLOOD wherein an apparatus similar to apparatus 10 is disclosed.

Typically, the whole blood is withdrawn from the donor at a volumetric rate of between 15 and 50 milliliters per minute and through empirical tests it has been found that a whole blood rate of withdrawal of approximately 30±5 milliliters per minute provides good results. Accordingly, the rate of withdrawal, i.e., the speed of the peristaltic pump 20 is started at a rate of 26 milliliters per minute.

As the whole blood is being drawn into the first separation chamber or receptacle 34, the centrifugal force acting on the receptacle 34 causes separation of the components of the whole blood. Platelet-rich plasma congregates in a zone at the top of the receptacle 34 adjacent to the outlet 36 and red blood cells congregate at the upper corners of the receptacle 34 adjacent outlets 40 and 42. This is achieved by the particular construction and orientation of the receptacle 34 which is described in more detail in a co-pending application Ser. No. 843,296 filed Oct. 18, 1977 and entitled: CENTRIFUGAL LIQUID PROCESSING SYSTEM.

The centrifuge device can be rotated at any one of several speeds of rotation from 0 to 1600 RPM. In a working example of the apparatus 10, a speed of 1400 RPM has been found to work very well. The speed of rotation of the centrifuge device 32 must be, of course, correlated with the distance of the two receptacles 34 and 53 from the axis of rotation of the centrifuge device 32 in order to obtain a desired "g" force on the blood fluid in the respective receptacles 34 and 53. In this respect, it has been found that a "g" force of between 150 and 600 "g's" provides good results, that is to say, a good separation of blood into its components. In a working example of the apparatus 10, the centrifuging takes place in the first and second receptacles 34 and 53 at approximately 285 "g's".

In the processing of whole blood it has been found best to process about 3 liters of blood at any one time. Accordingly, the controls for the apparatus 10 are set to process 3 liters of whole blood from the donor.

In light of the texture, size and number of particles in the blood, namely, red blood cells, white blood cells and platelets, whole blood does not strictly obey several known physical chemistry and fluid dynamic laws. Accordingly, the various operating parameters described herein have been determined more or less empirically. In this respect, it has been found that the efficiency of separation of plasma rich in platelets, referred to as platelet-rich plasma from the remainder of the whole blood in the receptacle 34 begins at a point when the hematocrit of the red blood cell rich blood fluid out of the outlets 40 and 42 from the receptacle 34 (hereinafter "hematocrit out") is approximately 56. Then, essentially 50% effectiveness of separation is obtained when the hematocrit out is 63. Finally, close to 100% effective and efficient separation of platelet-rich plasma from the whole blood blood occurs when the hematocrit is roughly 71.

With this relationship determined empirically, 285 "g's" on the first and second receptacles 34 and 53, provides a hematocrit out of approximately 70 and efficient separation of platelet-rich plasma from whole blood. Knowing this relationship, it has been determined that the ratio of the rates of withdrawal of whole blood out of the donor 14 and the rate of withdrawal of platelet-rich plasma from the receptacle 53 to obtain efficient separation and collection of platelets should be caused to approach the following formula:

$$\frac{V_{B1}}{V_{B1} - V_{PRP}} = \frac{\text{HEMATOCRIT}_{(BLOOD\ FLUID\ OUT)}}{\text{HEMATOCRIT}_{(BLOOD\ IN)}}$$

where:
$V_{B1}$ = volumetric flow in milliliters per minute of whole blood into the fluid circuit,
$V_{PRP}$ = volumetric flow in milliliters per minute of platelet-rich plasma withdrawn from the first receptacle 66,
HEMATOCRIT$_{(BLOOD\ FLUID\ OUT)}$ = concentration of red blood cells (by volume) per milliliter of blood fluid passing out of the first receptacle,
HEMATOCRIT$_{(BLOOD\ IN)}$ = concentration of red blood cells (by volume) per milliliter of fluid of the whole blood in.

With these relationships, and knowing that the typical hematocrit of the donor is 40, one can insert into the above formula the hematocrits of 40 and 70 and obtain a ratio of approximately 0.43, i.e., the rate of pumping of the platelet-rich plasma out of the receptacle 34 should be at roughly 43% of the rate of pumping of whole blood into the receptacle 34. In actual practice, however, this ratio will vary.

In one procedure for the operation of the apparatus 10 the volumetric rate of the pump 48 is started at a rate which is $(1 - \text{HEMATOCRIT}_{(WHOLE\ BLOOD\ IN)}) \times V_{B1}$. Since the hematocrit of the whole blood is roughly 40, this provides a starting speed for the pump 48 which is roughly 60% of the speed of pump 26. In one working example of the apparatus 10, the pump 26 is started at a speed which yields 26 milliliters per minute volumetric displacement. This ratio or relationship is maintained while the volumetric displacement of the pump 26 is increased 1 milliliter per minute after each 120 milliliters of whole blood, has been processed through the fluid circuit without a spillover of red blood cells. However, when a spillover of red blood cells from the receptacle 34 is sensed by the spillover detector device 50, pump 48 is stopped and then reversed to return the mixture of platelet-rich plasma and red blood cells to the receptacle 34. Then the speed of the pump 26 is decreased by one milliliter per minute and the speed of pump 48 is changed proportionately. Both pumps are then run in the normal direction (forward) until another 120 milliliters of whole blood is processed without a spillover. If a spillover is not detected by the spillover detector 50, the speed of the pump 48 is then increased by 0.25 milliliters per minute for each 120 milliliters of blood processed without a spillover until a spillover is detected. Then, when a spillover is detected, the pump 48 is again stopped and reversed to return the spillover mixture to the receptacle 34. Next, the volumetric displacement of the second pump 22 is decreased by 0.25 milliliters per minute and the pump 22 speed is reversed back to forward speed. This process is repeated until the end point is reached. By the end point is meant that the processing of approximately 3 liters of whole blood has been completed.

Operated in the above manner, the apparatus 10 has been found to provide a highly efficient and effective separation of platelet-rich plasma from whole blood; and the platelet-rich plasma which is withdrawn from the receptacle 34 is passed through the platelet receptacle 53 where, in view of the centrifugal force acting on the receptacle 53, platelet sedimentation occurs on the side of the receptacle or bag 53 while plasma flows through the bag 53.

It will be apparent from the foregoing description of the apparatus 10, that it is important to have a reliable, sensitive and efficient optical spillover detector 50 so that effective and efficient separation of platelet-rich plasma from whole blood is obtained. Such a reliable, sensitive, efficient and effective spillover detector 50 is obtained by constructing same according to the teachings of the present invention as described below and illustrated in FIGS. 2 and 3.

As shown in FIGS. 2 and 3, the spillover detector 50 includes a block 100 which has a generally rectangular cross section with rounded corners. In this particular embodiment, the block 100 has a generally oval cross section with oppositely facing flat sides 101 and 102 and oppositely facing rounded sides or ends 103 and 104.

The block 100 extends upwardly from and is integral with a generally rectangular base 106 which forms a mounting flange for the spillover detector 50. For this purpose the mounting flange 106 is provided with apertures 107 and 108 extending through the mounting flange 106 adjacent the opposite ends 103 and 104 of the block 100.

Also, the block 100 has formed therein a slot 110 which extends inwardly from a top surface 111 of the block 100 with an upper diverging portion 112 and an inner narrow portion 114 which has a width less than the outer diameter of the tubing 44 which is received into the slot 110. The tubing 44 is pushed into the inner portion 114 such that the tubing 44 is squeezed from a circular cross section to an oval cross section within the slot 110 as best shown in FIG. 3.

Referring now to FIG. 3, the block 100 has a first cavity or bore 121 therein which extends from the side 104 into the block 100 toward the slot 110 but not quite to the slot 110 such that a first sidewall 122 of the slot is defined between the inner end of the cavity 121 and the slot 110. In a like manner, a second cavity or bore 124 extends inwardly of the block 100 from the other side 104 toward the first cavity 121 but not quite to the slot 110 so that a second sidewall 126 of the slot 114 is defined between the inner end of the cavity 124 and the slot 110.

A third cavity or bore 128 is formed in the block 100 and extends upwardly from a recess 130 in the bottom of the block 100 to, and communicating with, the first cavity 121 and has an elongate axis 132. Also, a fourth bore 134 extends upwardly from the recess 130 and communicates with the second cavity or bore 124.

A "pen" lamp is received in the third cavity or bore 128. Typically, the lamp 140 is an inexpensive 1 to 2 watt lamp putting out 750 foot candles along the elongate axis thereof which is positioned coaxial with the axis 132 of the third cavity 128. Such a lamp is available under the trade name "Lens End Lamp".

The light from the lamp 140 is directed upwardly into the first cavity 120 and onto the surface of a reflecting member 142 positioned to reflect the light impinging thereon 90 degrees and through a first aperture 144 in the first sidewall 122, through a flat portion of the tubing 44, through the liquid flowing through the tubing 44, and then through a second aperture 146 in the second sidewall 126 into the second cavity 124 and to a photosensor 148. The photosensor 148 is a type 9 cadmium sulfide photocell which has a peak response at 550 nanometers, which functions as a photoresistor, which has a short response time, low drift and low memory and which is commercially available from Clairex Electronics, a division of Clairex Corporation of Mount Vernon, N.Y.

To prevent contamination of the components of the spillover detector 50, a first clear borosilicate glass (Pyrex T.M.) filter 151 is situated in the first cavity 120 adjacent the first sidewall 122 and fixed thereagainst, such as with an adhesive, to provide a seal between the slot 110 and the first cavity 120. Likewise, another clear borosilicate glass filter (Pyrex T.M.) 152 is situated in the second cavity 124 against the second sidewall 126 and fixed thereagainst, such as with an adhesive, to provide a seal between the slot 110 and the second cavity 124. In this way, any leakage of plasma or other liquid from the tubing 44 will not contaminate or interfere with the operation of the lamp 140 and the photosensor 148.

Also, between the pyrex filter 152 and the photosensor 148 is situated a colored glass filter 156, e.g., a blue green glass filter, that passes blue green light of 550 nm wavelength which is absorbed readily by oxygenated hemoglobin and which is not readily absorbed by other substances carried by the blood so that the photosensor 148 will quickly and accurately sense the spillover of red blood cells into the plasma flowing through the tubing 44 when there is a dropoff in the amount of blue green, 550 nm wavelength light sensed by the photosensor 148.

The block 100 is made of aluminum and has a mass sufficient to enable it to dissipate heat from the lamp 140 and prevent such heat from adversely affecting the operation of the photosensor 148. Also, it will be appreciated that the passage through the block defined by the second cavity 124, the fourth cavity 134 and the recess 130, allows ambient air to flow through the block to aid in the dissipation of heat. Moreover, dissipation of heat is aided by mounting the block by means of fasteners 161 and 162 received through apertures 107 and 108 to frame portion 163 and 164 adjacent a slot in a frame member of the apparatus 10. This configuration and mounting of the block 100 minimizes, if not altogether prevents, heat from the lamp 140 from adversely affecting the operation and sensitivity of the photosensor 148.

From the foregoing description it will be apparent that the spillover detector 50 of the present invention is of simple manufacture, utilizes inexpensive components and provides an efficient, reliable, low cost optical detector which is highly sensitive in sensing red blood cells mixed with plasma flowing through a tubing 44 received in the slot 110 of the optical spillover detector 50.

Further from the foregoing description, it will be apparent that the optical spillover detector 50 of the present invention has a number of advantages, some of which have been described above, e.g., such as heat dissipation, and others of which are inherent in the invention. Also, it will be apparent that obvious modifications can be made to the optical spillover detector 50 of the present invention without departing from the teachings of the present invention. Accordingly, the scope of the invention is only to be limited as necessitated by the accompanying claims.

We claim:

1. An optical density detector for sensing the change in optical density of a fluid flowing in a flexible, light transmitting tubing, said detector comprising a block having a slot across one face thereof, the inner portion of said slot having a width less than the outer diameter of the tubing which is received in said slot such that the tubing is squeezed from a circular cross section to an oval cross section with two respective flat portions adjacent opposite sidewalls of said slot, a first cavity in said block located behind a first sidewall of said slot and a second cavity in said block located behind a second sidewall of said slot, a first aperture in said first sidewall and a second aperture in said second sidewall, said apertures being coaxial, low power light generating means for directing light from said first cavity through said first aperture, through the flat portions of the tubing and through said second aperture into said second cavity and light sensing means in said second cavity for sensing the amount of light passed through the tubing and received in said second cavity and for generating an electrical signal which is indicative of the amount of light sensed and which can be utilized for measuring the optical density of the fluid flowing through the tubing, and said block being constructed in a manner to dissipate heat generated by said light generating means.

2. The detector according to claim 1 including first and second clear borosilicate glass filters, each fixed in one of said first and second cavities adjacent said first or second sidewall and each providing a fluid seal between said slot and said first or second cavity.

3. The detector according to claim 2 including a colored glass filter situated between said light sensing means and said clear borosilicate glass filter in said second cavity.

4. The detector according to claim 1 wherein said block has an elongate third cavity with an elongate axis normal to the axis of said apertures with one end opening into said first cavity, and wherein said light generating means includes an electrical lamp in said third cavity and a reflecting member mounted in said first cavity at an angle of 45 degrees, said elongate axis and said aperture axis intersecting at the surface of said reflecting member.

5. The detector according to claim 4 wherein said electric lamp received in said third cavity comprises a low wattage "pen" lamp which emits a strong light beam along the elongate axis thereof, said lamp being mounted in said elongate third cavity with said elongate axis thereof coaxial with said elongate axis of said third cavity.

6. The detector according to claim 5 wherein said lamp has a light output of approximately 750 foot candles at a power consumption of between 1 and 2 watts.

7. The detector according to claim 1 wherein said sensing means comprises a photosensor having a short response time, low drift and low memory.

8. The detector according to claim 1 particularly adapted for use with a blood separating apparatus of the type including a centrifuge for centrifuging whole blood to separate the whole blood into the components thereof and of the type wherein plasma is withdrawn from the centrifuge through the flexible tubing and wherein said detector is utilized to monitor the plasma being withdrawn from the centrifuge device and to detect the spillover of red blood cells into the plasma being withdrawn, and wherein said detector includes a blue green glass filter for passing blue green light at approximately 550 nonometers so that the detector is highly sensitive to the absorption of blue green light by oxygenated hemoglobin in red blood cells to quickly detect the spillover of red blood cells into the plasma.

9. The detector according to claim 8 wherein said light sensing means comprises a photosensor which has a short response time, low drift and low memory and which is highly sensitive to blue green light.

10. The detector according to claim 9 wherein said photosensor is a type 9 cadmium sulfide photocell having a peak response at approximately 550 nanometers.

11. The detector according to claim 1 wherein said block is made of a heat conductive material and has a mass sufficient to dissipate heat generated by said light generating means thereby to prevent such heat from adversely affecting the operation of said light sensing means.

12. The detector according to claim 11 wherein said block is made of a heat conducting material having a high thermal conductivity.

13. The detector according to claim 12 wherein said block has a mounting flange integral therewith which forms part of the heat dissipation structure of said block and which is adapted to be mounted to and between heat conducting frame members.

14. The detector according to claim 1 wherein said block includes a generally rectangular base integral therewith and forming a mounting flange, said slot being formed in the top face of said block and said block having four sides with said slot extending between one pair of oppositely facing sides and said first and second cavities being formed by coaxial bores extending into respective ones of the other pair of oppositely facing sides.

15. The detector according to claim 14 having a third bore extending upwardly from the bottom of said block to said first cavity.

16. The detector according to claim 15 having a fourth bore extending upwardly from the bottom of said block to said second cavity.

* * * * *